United States Patent [19]

Tsubaki et al.

[11] Patent Number: 4,666,637

[45] Date of Patent: May 19, 1987

[54] PROCESS FOR PRODUCING CHLOROBENZENE SULFOCHLORIDE

[75] Inventors: Kazumi Tsubaki; Noriaki Koto; Kouichi Maeda, all of Ichihara, Japan

[73] Assignee: Nissan Chemical Industries, Ltd., Tokyo, Japan

[21] Appl. No.: 788,671

[22] Filed: Oct. 17, 1985

Related U.S. Application Data

[63] Continuation of Ser. No. 494,672, May 13, 1983, abandoned, which is a continuation of Ser. No. 309,060, Oct. 6, 1981, abandoned.

[30] Foreign Application Priority Data

Oct. 14, 1980 [JP] Japan ............................... 55-143425

[51] Int. Cl.$^4$ .......................................... C07C 143/40
[52] U.S. Cl. .................................................. 260/543 R
[58] Field of Search .................................... 260/543 R

[56] References Cited

U.S. PATENT DOCUMENTS 3,108,137  10/1963  Barton et al. ................... 260/543 R

FOREIGN PATENT DOCUMENTS

| 483912 | 6/1952 | Canada | 260/543 R |
| 100035 | 8/1975 | Japan . | |
| 54-55548 | 5/1979 | Japan | 260/543 R |
| 162520 | 5/1964 | U.S.S.R. | 260/543 R |

*Primary Examiner*—Nicky Chan
*Attorney, Agent, or Firm*—Frishauf, Holtz, Goodman & Woodward

[57] ABSTRACT

A process for producing chlorobenzene sulfochloride comprises adding a reaction mixture of chlorobenzene and chlorosulfonic acid to water or diluted sulfuric acid to decompose excess chlorosulfonic acid; driving off hydrogen chloride thereby generated, from the system; bringing the sulfuric acid concentration in the sulfuric acid layer upon completion of the decomposition to be from 60 to 90%; and then separating chlorobenzene sulfochloride. The process is characterized in that the excess chlorosulfonic acid is decomposed at a temperature of from 40° to 85° C. and the chlorobenzene sulfochloride is separated in a liquid state at a temperature of from 60° to 80° C.

3 Claims, No Drawings

PROCESS FOR PRODUCING CHLOROBENZENE SULFOCHLORIDE

This application is a continuation of application Ser. No. 494,672, filed May 13, 1983, now abandoned, which was a continuation of Ser. No. 309,060 filed Oct. 6, 1981 (now abandoned).

The present invention relates to a process for producing chlorobenzene sulfochloride which comprises adding a reaction product (reaction mixture herein) of chlorobenzene and chlorosulfonic acid to water or diluted sulfuric acid thereby to decompose excess chlorosulfonic acid. Particularly, the present invention relates to a process for producing chlorobenzene sulfochloride, which comprises adding a reaction product of chlorobenzene and chlorosulfonic acid to water or diluted sulfuric acid to decompose excess chlorosulfonic acid, driving off hydrogen chloride thereby generated, from the system, bringing the sulfuric acid concentration in the sulfuric acid layer upon completion of the decomposition to be from 60 to 90%, separating chlorobenzene sulfochloride from the sulfuric acid layer in a liquid state at a temperature of not less than 50° C.

Chlorobenzene sulfochloride is commonly used as an intermediate for the production of monomers for polymer compounds, or as an intermediate for the production of pharmaceuticals or agricultural medicines.

In the production of chlorobenzene sulfochloride by the reaction of chlorobenzene and chlorosulfonic acid, the reaction formula is represented as follows:

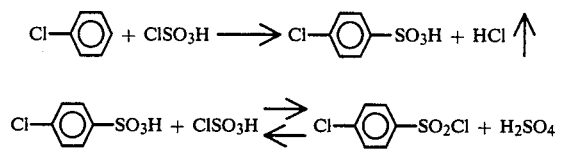

According to this reaction, hydrogen chloride gas and sulfuric acid are produced as by-products at the same time as the formation of the desired chlorobenzene sulfochloride. Further, the second stage reaction is an equilibrium reaction, and it is usual that an excess amount of chlorosulfonic acid is used to increase the yield of chlorobenzene sulfochloride. Thus, the reaction product usually contains, in addition to the above mentioned sulfochloride and sulfuric acid, unreacted chlorosulfonic acid and a small amount of chlorobenzene sulfonic acid. In order to separate the sulfochloride from such a reaction product, it is common to employ a method which comprises dumping the above mentioned reaction product into a great amount of cold water or ice water thereby to decompose the unreacted chlorosulfonic acid into hydrogen chloride and sulfuric acid, and separating the sulfochloride precipitated in the cold water in a solid form.

However, in the separation of the sulfochloride according to the above method, a great amount of water is used, and accordingly, hydrochloric acid and sulfuric acid formed by the hydrolysis of chlorosulfonic acid are thereby diluted, and thus it becomes difficult to reuse them as recovered hydrochloric acid and recovered sulfuric acid. Accordingly, a great amount of waste water is thereby formed, and the method has a great economical disadvantage. Further, in the separation of the sulfochloride according to the above mentioned method, the temperature of the system is rapidly raised by the generation of heat due to the hydrolysis reaction of the unreacted chlorosulfonic acid and by the heat of dilution of sulfuric acid contained in the reaction product as well as sulfuric acid produced by the hydrolysis of the chlorosulfonic acid. Accordingly, the method is considered to have a further disadvantage that the yield of the sulfochloride decreases as the desired sulfochloride undergoes a decomposition reaction due to the above mentioned heat.

Thus, when the above mentioned method is employed, it is common that the operation is carried out at a low temperature at a level of not more than about 30° C. in order to suppress the decomposition reaction of the sulfochloride, and a great amount of energy is required for the cooling.

Further, as an improved method for the production, there has been proposed a method which comprises adding a reaction product of an aromatic hydrocarbon and chlorosulfonic acid to diluted sulfuric acid thereby to decompose the excess amount of chlorosulfonic acid at a temperature of not more than 35° C., driving off hydrogen chloride thereby generated, from the system, bringing the sulfuric acid concentration in the sulfuric acid layer to be at least 70% and finally separating the aromatic sulfochloride from the sulfuric acid (Japanese Laid-Open Patent Application No. 100035/75), or a method in which hydrochloric acid of at least 20% is used instead of diluted sulfuric acid to suppress the heat of dilution of sulfuric acid, the excess amount of chlorosulfonic acid is decomposed at a temperature of not more than 35° C. and under conditions so that the sulfuric acid concentration in the sulfuric acid layer finally becomes not less than 70%, thereby releasing hydrogen chloride, and the cooling is effectively carried out taking advantage of the endothermic reaction of the releasing reaction (Japanese Laid-Open Patent Application No. 55548/79).

However, the desired chlorobenzene sulfochloride has a melting point of about 53° C., and if the above mentioned methods are used, the chlorobenzene sulfochloride forms a thick slurry solid at a temperature of not more than 35° C., and at a sulfuric acid concentration as high as at least 70%, it is very difficult to separate it by filtration, and yet the separated solid component would contain substantial amounts of sulfuric acid and unreacted chlorobenzene sulfonic acid, and thus it is required to use a great amount of cold water for the purification of the sulfochloride. With these drawbacks, the above methods are industrially extremely disadvantageous and unacceptable.

Having these points in mind, the present inventors have investigated the relation between the decomposition rate of chlorobenzene sulfochloride and the temperature by contacting the chlorobenzene sulfochloride which has a melting point of about 53° C. and which is solid at room temperature, with various concentrations of sulfuric acid. As a result, they have found a new fact that if the sulfuric acid concentration is from 60 to 90%, chlorobenzene sulfochloride does not substantially undergo decomposition even at a temperature higher than the temperature at which chlorobenzene sulfochloride forms a liquid phase, i.e. at a temperature higher than 50° C., and this is a discovery which breaks through the conventional general common knowledge. Thus, the present invention has been accomplished.

Namely, according to the present invention, a reaction product of chlorobenzene and chlorosulfonic acid is dropwise added to water or diluted sulfuric acid in an amount measured to bring the sulfuric acid concentration in the sulfuric acid layer after completion of the above mentioned decomposition to a level of from 60 to 90%, thereby to decompose excess chlorosulfonic acid. There is no particular restriction to the temperature at the time of the decomposition of the chlorosulfonic acid. However, in order to efficiently effect the decomposition, a proper temperature may be selected within a range from 50° C. to 85° C. It is preferred that the temperature is selected within a range of from 50° C. to 75° C. at which a small amount of a precipitate forms or the system is completely in a liquid state during the decomposition. Within this temperature range, the sulfochloride undergoes substantially no decomposition. As an example, Table 1 shows decomposition rates obtained by contacting chlorobenzene sulfochloride with sulfuric acid of various concentrations. Namely, 5 parts of chlorobenzene sulfochloride, the purity of which was preliminarily determined, was added in 50 parts of sulfuric acid having various concentrations as shown in Table 1 and stirred at 65° C. for 2 hours, and thereafter the decomposition rate of the chlorobenzene sulfochloride was measured.

TABLE 1

| Concentration of sulfuric acid (% by weight) | 50 | 60 | 65 | 75 | 85 | 97 |
|---|---|---|---|---|---|---|
| Decomposition rate (%) | 3.9 | 2.1 | 0.8 | 1.2 | 2.4 | 20 |

From the above results, it can be said that if the concentration of the sulfuric acid to be contacted, is from 60 to 90%, the chlorobenzene sulfochloride undergoes substantially no decomposition even at 65° C.

Thus, it is possible to carry out the decomposition of the excess chlorosulfonic acid in the reaction product of chlorobenzene and chlorosulfonic acid, at such a high temperature. Accordingly, the cooling operation from outside can thereby be simplified, and the time for the decomposition can be shortened. After completion of the decomposition of excess chlorosulfonic acid, if necessary, air or nitrogen may be blown in to drive off hydrogen chloride from the system. Then, the sulfuric acid layer and the chlorobenzene sulfochloride layer can readily be separated in a liquid state at 60° C. to 80° C., preferably at 60° to 75° C., without substantial decomposition of chlorobenzene sulfochloride.

The chlorobenzene sulfochloride layer thus separated has an adequately high purity as chlorobenzene sulfochloride by itself, i.e. without being further purified, and the amounts of the remaining sulfuric acid and chlorobenzene sulfonic acid are minimal.

However, when it is used for fine synthetic reactions, it is required to further improve the purity. According to the process of the present invention it becomes possible to carry out more effectively a purification method which is free from a loss of the chlorobenzene sulfochloride separated from the sulfuric acid layer and which does not bring about a waste. Namely, the purification can readily be done simply by dissolving the chlorobenzene sulfochloride layer separated from the sulfuric acid layer in an inert organic solvent and thereafter washing it with a small amount of water, and, besides, all of the waste water after the washing, can be used as the water component for decomposing the excess chlorosulfonic acid in the reaction product of chlorobenzene and chlorosulfonic acid, or as the water component for preparing the diluted sulfuric acid to be used for the same purpose, and it is thereby possible to produce chlorobenzene sulfochloride in the same efficiency as in the case where pure water is used. This is an advantage obtainable by the process of the present invention.

Namely, the present invention makes it possible further to produce superiorly purified chlorobenzene sulfochloride, without any waste water to be formed in the production of the purified chlorobenzene sulfochloride.

The inert organic solvent to be used in the above purification step is a solvent in which clorobenzene sulfochloride is adequately soluble without being decomposed, and which is insoluble or hardly soluble in water. For example, an aliphatic saturated hydrocarbon, an aromatic hydrocarbon, a halogenated aliphatic hydrocarbon and a halogenated aromatic hydrocarbon are used. Specific examples are hexane, heptane, octane, benzene, toluene, xylene, methylene chloride, chloroform, dichloroethane, trichloroethane, chlorobenzene and dichlorobenzene.

Further, the small amount of water to be used for washing the solution prepared by adding the inert organic solvent to the chlorobenzene sulfochloride layer, is meant for water in an amount of from 10 to 100 g per 100 g of the chlorobenzene sulfochloride layer and which is less than the amount of water required to decompose the excess chlorosulfonic acid in the reaction product of chlorobenzene and chlorosulfonic acid and to eventually bring the sulfuric acid concentration in the sulfuric acid layer to a level of from 60 to 90%. If the amount of water is within the above range, no waste water will be formed at the time of obtaining the purified chlorobenzene sulfochloride.

Namely, the waste water after the washing operation can all be reused as the water component for the decomposition of the excess chlorosulfonic acid in the reaction product of chlorobenzene and chlorosulfonic acid, or as the water component for the preparation of the diluted sulfuric acid to be used for the same purpose. Accordingly, in this purification step, no waste water will be formed.

Further, after separating the chlorobenzene sulfochloride layer in a liquid state, the obtained sulfuric acid layer is cooled and the precipitate is separated. The separated precipitate can be reused as it is or after subjecting it to azeotropic dehydration with chlorobenzene, as a feed material for the preparation of the reaction product of chlorobenzene and chlorosulfonic acid. It has been found that the yield of chlorobenzene sulfochloride per chlorobenzene used, can thereby be increased. Further, the purity of sulfuric acid is thereby improved, and thus the value of the regenerated sulfuric acid is increased for reutilization. This is another advantage obtainable by the process of the present invention.

As mentioned above, according to the process of the present invention, the following useful results are obtainable.

(1) Chlorobenzene sulfochloride does not substantially undergo decomposition even when contacted with from 60 to 90% of sulfuric acid at a temperature higher than the temperature at which the sulfochloride turns into a liquid phase. Therefore, the sulfuric acid layer and the chlorobenzene sulfochloride layer can readily be separated in a liquid state.

(2) When the excess chlorosulfonic acid in the reaction product of chlorobenzene and chlorosulfonic acid is hydrolyzed, the temperature for the hydrolysis can be brought higher than room temperature, preferably to a high level of from 40° to 75° C. The cooling operation from outside such as temperature control can be simplified, and the time required for the hydrolysis can be shortened, thus bringing about an economical advantage.

(3) The chlorobenzene sulfochloride separated in a liquid state, contains minimal amounts of sulfuric acid and chlorobenzene sulfonic acid. Therefore, the purification operation to obtain a highly pure product can readily be made, and brings about little waste which requires after-treatment. Thus, the economical merits thereby obtainable are substantial.

(4) As the sulfuric acid generated as a by-product can be recovered at a high concentration of from 60%–90%, it is possible to reuse the sulfuric acid for other usages.

(5) The hydrogen chloride generated as a by-product, does not accompany any substance having a low vapour pressure such as an organic solvent, and accordingly it can be recovered as highly pure hydrochloric acid and can therefore be reused.

(6) The waste water after the washing operation can all be reused as the water component for the decomposition of the excess chlorosulfonic acid in the reaction product of chlorobenzene and chlorosulfonic acid, or as the water component for the preparation of the diluted sulfuric acid to be used for the same purpose. Thus, this purification step yields no waste water.

(7) The major proportion of the precipitate obtained by cooling the sulfuric acid layer is unreacted chlorobenzene sulfonic acid, which can be used as the feed material for the preparation of the reaction product of chlorobenzene and chlorosulfonic acid. Thus, it is possible to increase the yield of chlorobenzene sulfochloride per chlorobenzene used.

(8) The major proportion of unreacted chlorobenzene sulfonic acid is removed from the sulfuric acid layer, and accordingly, the purity of the sulfuric acid is thereby improved and the value of the regenerated sulfuric acid is increased for reutilization. The regenerated sulfuric acid can be reused as a feed material for the preparation of the diluted sulfuric acid which is used for the decomposition of the excess chlorosulfonic acid.

Now, the invention will be described in further detail with reference to Examples and Comparative Examples. However, it should be understood that the present invention is not limited to these Examples.

EXAMPLE 1

Fed into a flask was 524 g (4.5 moles) of chlorosulfonic acid, and then 169 g (1.5 moles) of chlorobenzene was dropwise added thereto while cooling the system to maintain it at a temperature of not more than 60° C. It took about 30 minutes to complete the dropwise addition, and then the system was kept at 60° C. for 2 hours. Then, the reaction product thereby obtained was dropwise added to 140 g of water at a temperature of from 40° to 60° C. for 20 minutes. After the completion of the dropwise addition, the reaction was aged at a temperature of from 60° to 65° C. for 20 minutes, and then dried air was continuously blown into the reaction product to drive off the remaining hydrogen chloride from the system. Thereafter, the reaction product was transferred to a dropping funnel which was kept warm, and the liquid phase separation was carried out at a temperature of 65° C. The lower layer was a sulfuric acid layer, from which 424 g of sulfuric acid having a concentration of 73% was recovered. The upper layer was a chlorobenzene sulfochloride layer, from which 289 g of chlorobenzene sulfochloride having a purity of 90% was obtained. The yield based on the feed chlorobenzene was 82%.

EXAMPLE 2

The operation was carried out in the same manner as in Example 1 except that the reaction product of chlorosulfonic acid and chlorobenzene was dropwise added to 788 g of 60% sulfuric acid. After the liquid phase separation, about 1100 g of sulfuric acid having a concentration of 73% was obtained from the lower layer. From the upper layer, 286 g of chlorobenzene sulfochloride having a purity of 92% was obtained. The yield based on the feed chlorobenzene was 83%.

EXAMPLE 3

The operation was carried out in the same manner as in Example 1 except that the reaction product of the chlorosulfonic acid and chlorobenzene was dropwise added to 284 g of 60% sulfuric acid.

After the liquid phase separation, about 600 g of sulfuric acid having a concentration of 85% was recovered from the lower layer. From the upper layer, 279 g of chlorobenzene sulfochloride having a purity of 92% was obtained from the upper layer. The yield based on the feed chlorobenzene was 81%.

EXAMPLE 4

The operation was carried out in the same manner as in Example 1 except that the reaction product was dropwise added to 683 g of 40% sulfuric acid.

After the liquid phase separation, about 1000 g of sulfuric acid having a concentration of 60% was recovered from the lower layer. From the upper layer, 286 g of chlorobenzene sulfochloride having a purity of 92% was obtained. The yield based on the feed chlorobenzene was 83%.

EXAMPLE 5

The operation was carried out in the same manner as in Example 2 except that the temperature for the liquid phase separation of the sulfuric acid layer and the chlorobenzene sulfochloride layer was 75° C.

After the liquid phase separation, about 1100 g of sulfuric acid having a concentration of 73% was recovered from the lower layer. From the upper layer, 282 g of chlorobenzene sulfochloride having a purity of 91% was obtained. The yield based on the feed chlorobenzene was 81%.

EXAMPLE 6

The operation was carried out in the same manner as in Example 2 except that the temperature for the liquid phase separation of the sulfuric acid layer and the chlorobenzene sulfochloride layer was 50° C.

After the liquid phase separation, about 1100 g of sulfuric acid having a concentration of 73% was recovered from the lower layer. From the upper layer, 289 g of chlorobenzene sulfochloride having a purity of 91% was obtained. The yield based on the feed chlorobenzene was 83%.

COMPARATIVE EXAMPLE 1

The operation was carried out in the same manner as in Example 1 except that the reaction product of chlorosulfonic acid and chlorobenzene was dropwise added to 128 g of 60% sulfuric acid.

After the liquid phase separation, about 450 g of sulfuric acid having a concentration of 95% was recovered from the lower layer. From the upper layer, 253 g of chlorobenzene sulfochloride having a purity of 85% was obtained. The yield based on the feed chlorobenzene was 68%. It is seen that the yield as well as the purity is considerably inferior to the Examples of the present invention.

COMPARATIVE EXAMPLE 2

The operation was carried out in the same manner as in Example 1 except that the reaction product of chlorosulfonic acid and chlorobenzene was dropwise added to 1628 g of 40% sulfuric acid.

After the liquid phase separation, about 1960 g of sulfuric acid having a concentration of 50% was recovered from the lower layer. From the upper layer, 267 g of chlorobenzene sulfochloride having a purity of 90% was obtained. The yield based on the feed chlorobenzene was 76%, which is considerably inferior to the Examples of the present invention.

COMPARATIVE EXAMPLE 3

A reaction product of chlorosulfonic acid and chlorobenzene, was prepared in the same manner as in Example 1. Then, the reaction product was dropwise added to 788 g of 60% sulfuric acid while maintaining the temperature of the system at a level of at most 25° C. Immediately after the commencement of the dropwise addition, the system turned into a slurry state, and finally became a thick slurry, whereby the stirring and the cooling were very difficult. Accordingly, it required 2 hours for the dropwise addition of the whole amount. After the completion of the dropwise addition, dry air was continuously blown into the product to drive off the remaining hydrogen chloride from the system.

Thereafter, the reaction product was filtered at 25° C., and sulfuric acid was sufficiently squeezed out, whereupon about 1030 g of sulfuric acid having a concentration of 73% was recovered. The filtered product was chlorobenzene sulfochloride having a purity of 72%, and the amount thereof was 360 g. The yield based on the feed chlorobenzene was 82%. It is seen that the purity is considerably lower than the Examples of the present invention.

We claim:

1. A process for producing chlorobenzene sulfochloride comprising reacting chlorobenzene and chlorosulfonic acid to provide a reaction mixture containing chlorobenzene sulfochloride, hydrogen chloride, sulfuric acid and excess chlorosulfonic acid;

adding said reaction mixture to water or diluted sufuric acid to decompose said excess chlorosulfonic acid and to form a chlorobenzene sulfochloride layer and a sulfuric acid layer having a sulfuric acid concentration of from 60 to 90% after completion of said decomposition, said decomposition being carried out at a temperature of from 50° to 85° C., and driving off remaining hydrogen chloride from the system; and separating said chlorobenzene sulfochloride layer in the liquid state at a temperature from 60° to 80° C.

2. The process as claimed in claim 1, wherein the separation temperature is from 60° to 75° C.

3. The process as claimed in claim 1, wherein said decomposition is carried out at a temperature of not more than 75° C.

* * * * *